United States Patent [19]

Wiktorowicz

[11] Patent Number: 5,015,350
[45] Date of Patent: May 14, 1991

[54] FLOW-RATE-CONTROLLED SURFACE-CHARGE COATING FOR CAPILLARY ELECTROPHORESIS

[75] Inventor: John E. Wiktorowicz, San Jose, Calif.
[73] Assignee: Applied Biosystems, Inc., Foster City, Calif.
[21] Appl. No.: 432,061
[22] Filed: Nov. 6, 1989
[51] Int. Cl.⁵ ............................................. G01N 27/26
[52] U.S. Cl. ............................. 204/180.1; 204/180.7; 204/181.4; 204/182.2; 204/182.8; 204/183.3; 204/299 R; 427/230
[58] Field of Search ............... 204/180.1, 182.2, 182.8, 204/183.3, 299 R, 180.7, 181.4; 427/230

[56] References Cited

U.S. PATENT DOCUMENTS

| | | | |
|---|---|---|---|
| 3,909,380 | 9/1975 | Day et al. | 204/180.1 |
| 4,680,201 | 7/1987 | Hjerten | 427/230 |
| 4,865,706 | 9/1989 | Karger et al. | 204/182.8 |
| 4,865,707 | 9/1989 | Karger et al. | 204/180.1 |

OTHER PUBLICATIONS

Cohen, A. S. et al., Anal. Chem. 59:1021 (1987).
Cohen, A. S. et al., J. Chromatography 458:323 (1988).
Compton, S. W. et al., Biotechniques 6(5):432 (1988).
Lauer, H. H. et al., Anal. Chem. 58:166 (1986).
Kasper, T. J. et al., J. Chromatography 458:303 (1988).
McCormick, R. M. et al., Anal. Chem. 60(21):2322 (1988).
Herren, B. J. et al., J. Colloid and Interface Sci. 115(1):46 (1987).
Somasundaran, P. et al., J. Physical Chem. 68(12):3562 (1984).

Primary Examiner—T. Tung
Assistant Examiner—David G. Ryser
Attorney, Agent, or Firm—Peter J. Dehlinger; Joseph H. Smith

[57] ABSTRACT

A method for achieving desired electroosmotic flow characteristics in a capillary tube having charged surface groups. An electrolyte solution containing a compound effective to stably alter the charge of the tube walls is drawn into and through the tube during while the electroosmotic flow rate in the tube is being monitored, until a desired electroosmotic flow rate is achieved. The method can be used to optimize electrophoretic separation of charged protein or nucleic acid species in a capillary tube, and to produce capillary tubes with desired charge density properties.

16 Claims, 8 Drawing Sheets

FLOW-RATE-CONTROLLED SURFACE-CHARGE COATING FOR CAPILLARY ELECTROPHORESIS

FIELD OF THE INVENTION

The present invention relates to capillary electrophoresis, and in particular, to methods for achieving controlled electroosmotic flow rates in a capillary tube, for enhancing electrophoretic separation of biomolecules.

REFERENCES

Cohen, A. S., et al, Anal Chem, 59:1021 (1987).
Cohen, A. S., et al, J. Chromatography, 458:323 (1988).
Compton, S. W., et al BioTechniques, 6(5):432 (1988).
Herrin, B. J., J Colloid Interface Sci, 115(1):46 (1987).
Kaspar, T. J., et al, J Chromatography, 458:303 (1988).
Lauer, H. H., Anal Chem, 58:166 (1985).
McCormick, R. W., Anal Chem, 60(21):2322 (1988).

BACKGROUND OF THE INVENTION

Capillary electrophoresis (CE) has been proposed for rapid fractionation of a variety of biomolecules (Cohen, 1987, 1988, Compton, Kaspar). In the usual CE procedure, the capillary tube is filled with an electrophoresis medium, a small sample volume is drawn into one end of the tube, and an electric field is placed across the tube to draw the sample through the medium. The electrophoretic medium may be a non-flowable polymer or gel material such as agarose gel, but, for many types of separation, may be a flowable fluid medium. Electrophoretic separation of proteins in a fluid electrophoretic medium, based on the differential charge density of the protein species, has been reported (Lauer). For fractionation of nucleic acid species (which have similar charge densities, and therefore must be separated on the basis of size alone) it has been found that high-resolution fractionation can be achieved in a fluid electrophoretic medium containing high molecular weight polymers. This method is described in co-owned U.S. patent application for "Nucleic Acid Fractionation by Counter-Migration Capillary Electrophoresis", Ser. No. 390,631, filed Aug. 7, 1989.

When CE is carried out using a fluid electrophoretic medium, the medium itself may undergo bulk flow migration through the capillary tube toward one of the electrodes. This electroosmotic flow is due to a charge shielding effect produced at the capillary wall interface. In the case of standard fused silica capillary tubes, which carry negatively charged silane groups, the charge shielding produces a cylindrical "shell" of positively charged ions in the electrophoresis medium near the surface wall. This shell, in turn, causes the bulk flow medium to assume the character of a positively charged column of fluid, and migrate toward the cathodic electrode at an electroosmotic flow rate which is dependent on the thickness (Debye length) of the shell.

Electroosmotic flow rate may provide a important variable which can be optimized to improve separation among two or more similar species, as has been described in the above-cited patent application. In particular, when CE is carried out under conditions in which electroosmotic flow occurs in one direction, and the migration of the species to be separated is in an opposite direction, the effective column length for separation for any given species can be made extremely long by making the electroosmotic flow rate in one direction nearly equal to the electrophoretic migration rate of that species in the opposite direction.

Heretofore, attempts to modulate or control electroosmotic flow rate in CE have been limited. In one approach, the pH of the electrophoretic medium is made sufficiently low, e.g., less than pH 2-4, to protonate charged surface groups, and thus reduce surface charge density This approach is not applicable to many proteins where low-pH denaturation effects can occur.

It has also been proposed to include in the electrophoretic buffer, a charged agent which can bind to the surface at a given equilibrium constant, to mask surface charge, and thus reduce electroosmotic flow. This approach is severely limited by the problem of the charged agent binding to the species to be separated, thus altering the charge density and migration characteristics of these species Also, the concentration of binding compound must be calibrated by trial and error.

Attempts to reduce or eliminate electroosmotic flow by covalently derivatizing the charged surface groups in a CE tube with neutral or positively charged agents has also been reported. This approach suffers from the difficulty in calibrating the reaction conditions to achieve a desired electroosmotic flow. In addition, the derivitization reaction is irreversible, i.e., the tube cannot be recoated to achieve other selected electroosmotic flow rates.

SUMMARY OF THE INVENTION

It is one general object of the invention to provide a rapid, simple method for achieving a selected electroosmotic flow rate in a CE tube.

A more specific object is to provide such a method which is easily performed, compatible with both protein and nucleic acid CE fractionation, and which may be carried out in a manner which results in either reversible or irreversible surface charge densities in a CE tube.

The invention includes, in one aspect, a method of achieving selected electroosmotic flow characteristics in a capillary tube having charged surface groups. The tube is connected between anodic and cathodic electrolyte reservoirs, and an electric field is placed across the reservoirs to produce electroosmotic flow within the tube. During electroosmotic flow, a compound capable of stably altering the surface charge of the tube is drawn into and through the tube, and the electroosmotic flow rate within the tube is monitored Drawing the compound into and through the tube is continued until a desired electroosmotic flow rate in the tube, as determined from the monitoring, is achieved.

The electroosmotic flow rate through the tube is preferably monitored by introducing into the tube, at selected time intervals, a series of pulses of a flow marker whose travel through the tube can be used to monitor the electroosmotic flow rate of a band of fluid in the tube containing the marker solution.

In one general embodiment, the capillary tube is a fused silica tube having negatively charged surface silane groups, and the charge-altering compound is a polymer containing regularly spaced, charged amine groups, and preferably a hydrophobic polymer with quaternary amine charged groups, such as the polymer polybrene.

In another general embodiment, the capillary tube is a glass tube having positively charged amine groups, and the charge-altering compound is a negatively charged polymer, such as a polymer of polysulfonic acid, polycarboxylic acid, polyphosphonic acid, or polyphosphoric acid.

Where a charged, hydrophobic polymer, such as a hydrophobic polyamine, is used, the method may be practiced to achieve a selected degree of overcoating which produces electroosmotic flow in a reverse direction. In this method, the polymer is first drawn through the tube in the initial direction of electroosmotic flow, until the charge on the surface walls is neutralized and electroosmotic flow in the initial direction ceases. Thereafter, the compound is drawn into and through the tube in the same direction by electrophoresis, until electroosmotic flow within the tube in the opposite direction reaches a selected rate. This method is useful for separating positively charged proteins since (a) the net positive charge of the tube walls prevents nonspecific electrostatic protein binding to the wall surfaces, and (b) the reverse-direction rate of electroosmotic flow can be selected to optimize protein separation.

The method of the invention may further include a step for producing a capillary tube having a selected density of covalently attached charged groups on the surface of the capillary wall, using a compound which has chemical groups both for masking wall surface charge and for covalent attachment to reactive chemical groups on the tube wall. After achieving the desired electroosmotic flow, the coated tube is treated with a coupling agent effective to couple the compound covalently to the surface walls.

In another aspect, the invention includes a CE tube formed by the method of the invention. The tube is characterized by a (a) selected electroosmotic flow, in a given electrophoresis medium, and (b) a coating of a charged polymer agent. In one preferred embodiment, the charged agent is a hydrophobic polyquaternary amine polymer.

These and other objects and features of the invention will become more fully apparent when the following detailed description of the invention is read in conjunction with the accompanying drawings.

DETAILED DESCRIPTION OF THE INVENTION

I. Capillary Electrophoresis System

Figure 1:
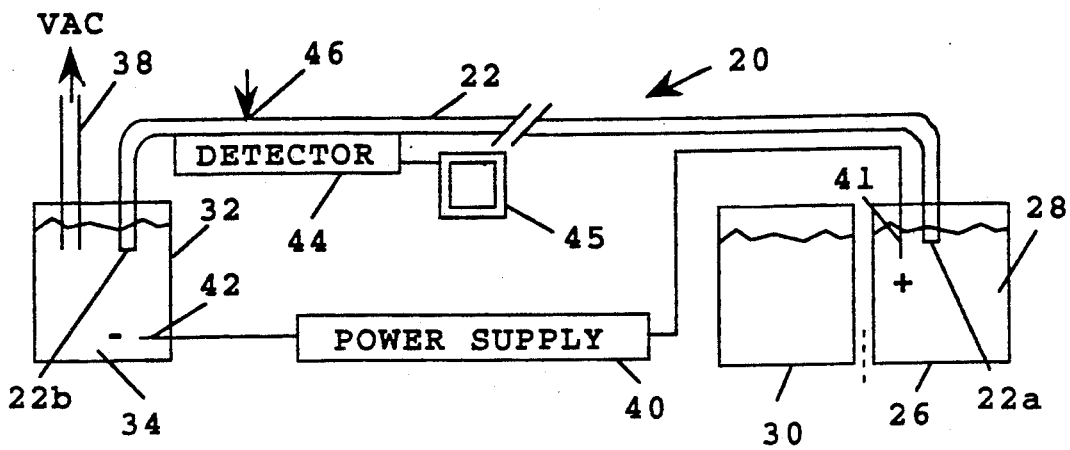
FIG. 1 is a schematic diagram of a capillary electrophoresis system used in practicing the method of the present invention.

FIG. 1 is a simplified schematic view of a capillary electrophoresis (CE) system 20 suitable for practicing the flow-rate controlled surface-charge coating (FCSC) method of the invention. The system is also suitable for carrying out electrophoretic separations using tubes prepared by the FCSC method. The system includes a capillary tube 22 having a length preferably between about 10–200 cm, typically less than about 100 cm, and an inner diameter of preferably between about 25–200 $\mu$m (microns), typically about 50 $\mu$m. In the embodiment shown, the tube is supported in a horizontal position and has downwardly bent end regions.

The inner surface of the tube has chemical groups which are either negatively or positively charged, typically at a pH of between about 2–11. The surface chemical groups may be an inherent property of the capillary material, such as is the case for a fused silica tube which has surface silane groups resulting in a negative charge. Alternatively, or in addition, the capillary walls may be treated with known derivatization reagents for attachment of chemical groups, such as quaternary amines, to the inner capillary walls, or with known positively charged surface-coating agents. More generally, the capillary tube may be any tube or channel capable of supporting a column of buffer, preferably at a column thickness of 200 $\mu$m or less. For example, the tube may take the form of a channel formed in a glass slide or the like, and having negatively charged surface groups. One preferred capillary tube is a fused silica tube having an inner diameter of 50 $\mu$m and available from Polymicro Technologies (Phoenix, AZ), and a negatively charged surface wall.

An anodic reservoir 26 in the system contains an electrolytic solution 28 which is drawn through the tube by electroosmotic flow (Section II) with the application of an electric field across the tube ends. The anodic end of the tube, indicated at 22a, is immersed in the solution, as shown, during electrophoresis.

A reservoir 30 in the system may contain a marker solution, for use during the FCSC method, or may contain a sample of molecules to be separated, during an electrophoretic separation. Preferably the marker or sample material is dissolved in the electrolytic solution or in water. The two anodic reservoirs may be carried on a carousel or the like, for placement at a position in which the lower anodic end of the tube can be immersed in the reservoir fluid. Although not shown here, the carousel may carry additional reservoirs containing solutions for cleaning and flushing the tube between electrophoretic runs or different solutions, where two or more solutions are employed in a single electrophoretic fractionation method.

The opposite, cathodic end of the tube, indicated at 22b, is sealed within a cathodic reservoir 32 and is immersed in an cathodic electrolyte solution 34 contained in the reservoir, as shown. A second tube 38 in the reservoir is connected to a finely-controlled vacuum system (not shown) for drawing fluid, (e.g., washing and cleaning solutions, marker solution, and electrophoresis buffer solution) through the tube and for loading the macromolecule sample material in reservoir 30 into the tube.

A high voltage supply 40 in the system is connected to the anodic and cathodic reservoirs as shown, for applying a selected electric potential between the two reservoirs. The power supply leads are connected to platinum electrodes 41, 42 in the anodic and cathodic reservoirs, respectively. The power supply may be designed for applying a constant voltage (DC) across the electrodes, preferably at a voltage setting of between 5-50 KV. Alternatively, or in addition, the power supply may be designed to apply a selected-frequency, pulsed voltage between the reservoirs. The polarity of power supply output can be reversed. In general, the shorter the capillary tube, the higher the electric field strength that can be applied, and the more rapid the electrophoretic separation.

When operated in a pulsed voltage mode, the power supply preferably outputs a square wave pulse at an adjustable frequency of about 50 Hz up to a KHz range, and an rms voltage output of about 10-30 KV. Higher pulse frequencies, even into the MHz range may be suitable for some applications.

Completing the description of the system shown in FIG. 1, a detector 44 in the system is positioned adjacent the cathodic end of the tube, for optically monitoring marker or sample material migrating through an optical detection zone 46 in the tube. The detector may be designed either for UV absorption detection and/or for fluorescence emission detection. UV absorbance is typically carried out at 200-280 nm, using, for example, a Kratos 783 UV absorbance detector which has been modified by Applied Biosystems (Foster City, CA.), by replacing the flow cell with a capillary holder. Fluorescence emission detection is preferably carried out at a selected excitation wavelength which is adjustable between about 200-500 nm, depending on the fluorescent species associated with the marker or sample material, as discussed below One exemplary fluorescence detector is an HP1046A detector available from HewlettPackard (Palo Alto, CA), and modified as above for capillary tube detection. The detector is connected to an integrator/plotter 45 for recording electrophoretic peaks.

Using the detector shown in FIG. 1, the electroosmotic flow rate measured during the FCSC method is determined by calculating the time required for a marker band to travel from the upstream end (end 22a) of the tube to the detection zone tube, near the tube's downstream end. The electroosmotic flow rate detected in this manner thus represents an average of the instantaneous flow rates at the time the marker is introduced into the tube and at the time the marker is detected. It will be appreciated that the system can be modified to allow determination of an instantaneous flow rate, by placing directly upstream of the detector, a T-tube through which marker can be periodically introduced into the tube.

Figure 2:
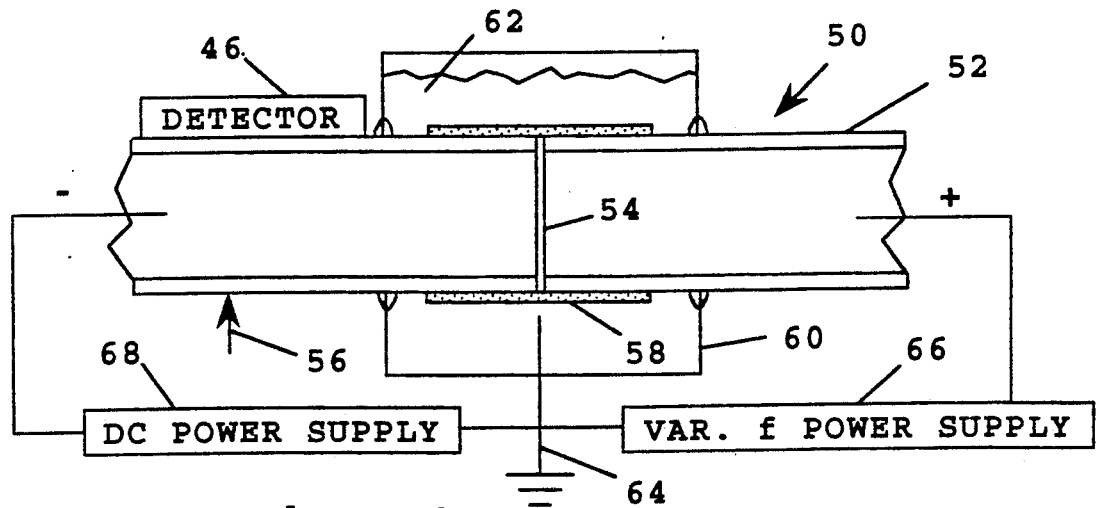
FIG. 2 is a schematic view of a capillary electrophoresis system designed for operation simultaneously in both a pulsed and constant-voltage mode; pulsed and constant-voltage mode.

FIG. 2 shows a fragmentary view of an electrophoretic system 50 which can be operated in both a pulsed and constant-voltage mode. The capillary tube 52 in the system has a small-clearance break 54 adjacent and upstream of the detection zone, indicated at 56. The tube sections on either side of the break are coupled by a porous glass sleeve 58 which allows electrolyte migration into and out of the tube. The coupled portion of the tube is sealed within a reservoir 60 filled with a suitable electrolyte solution 62. A grounded electrode 64 in the reservoir is connected to the high-voltage side of a pulsed-voltage power supply 66 whose negative side is in communication with a suitable cathodic reservoir. The grounded electrode 64 is connected to the high-voltage side of a DC power supply 68 whose negative side is in communication with a suitable anodic reservoir.

II. Electroosmotic Flow

This section describes the phenomenon of electroosmotic flow. The phenomenon is exploited both in the FCSC method of the invention, for achieving a desired surface charge coating in the electrophoresis tubes, and in an electrophoretic separation of sample material.

Figure 3:
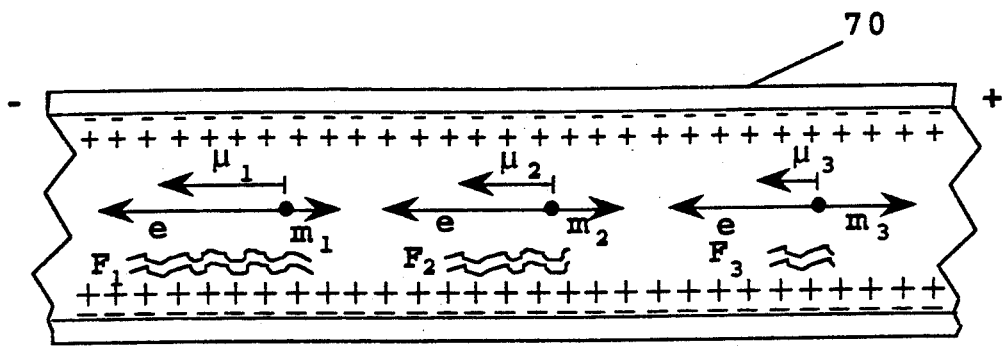
FIG. 3 is an enlarged, fragmentary portion of a capillary electrophoresis tube, illustrating electroosmotic flow (e) in a left-to-right direction, and fragment migration ($m_1$, $m_2$, $m_3$) in a right-to-left direction.

FIG. 3 shows an enlarged, fragmentary portion of a capillary electrophoresis tube 70. As seen in the figure, the negatively charged groups on the inner tube wall, indicated by "−" symbols, are shielded by positively charged ions in the polymer solution, essentially forming a positively charged shell about the column of fluid in the tube. Under the influence of an electric field, this column of polymer solution in the medium (which is surrounded by a shell of positive charges) is drawn electroosmotically in the direction of negative or low potential. The rate of electroosmotic flow in the tube is indicated by the arrow e in the figure (arrow e may be thought of as a vector with a magnitude e and a direction along the axis of the tube). The electroosmotic flow rate e in a capillary tube can be described by the equation:

$$e = \frac{\epsilon \zeta E}{\eta}$$

where $\epsilon$, $\eta$, $\zeta$, and E are the permittivity of the fluid, its viscosity, the zeta potential, and the electrical field strength, respectively.

The zeta potential, $\zeta$, as it applies to a charged wall surface, describes the potential across the interfacial double layer between the charged wall surface and the "inner surface" of the charged shell corresponding to the radius of shear of the shell. The $\zeta$ potential is directly dependent on the net charge of the wall surface, and can be increased or decreased by increasing or decreasing the wall surface charge density, respectively.

FIG. 3 also illustrates how electrophoretic separation of sample species, such as the three negatively charged species shown at $F_1$, $F_2$, and $F_3$ can be enhanced in a CE tube which is prepared, according to the present invention, to provide a selected electroosmotic flow rate. Here the rate of electroosmotic flow is indicate by a vector e, indicating a magnitude e in the downstream direction in the figure. The three species migrate electrophoretically in the opposite direction at rates by the vectors indicated at $m_1$, $m_2$, and $m_3$. The net rate of migration of each species in the tube is the sum of the two opposing vectors, indicated by $\mu_1$, $\mu_2$, and $\mu_3$, respectively.

It can be appreciated that the ability to separate the three species depends on the differences between the three net migration-rate vectors $\mu_1$, $\mu_2$, and $\mu_3$. The relative differences between these vectors, in turn, can be selectively controlled by varying e. For example, by making e close to $m_3$, the vector $\mu_3$ can be made quite small and thus allow $F_3$ to be readily separated from the other two species. Likewise, by making e quite close to $m_2$, the vector $\mu_2$ can be made quite small and thus allow $F_2$ to be readily separated from $F_1$.

The use of selected electroosmotic flow rate to optimize protein and nucleic acid separations will be described in more detail below.

III. Flow-Rate Controlled Surface-Charge Coating (FCSC)

Figure 4:
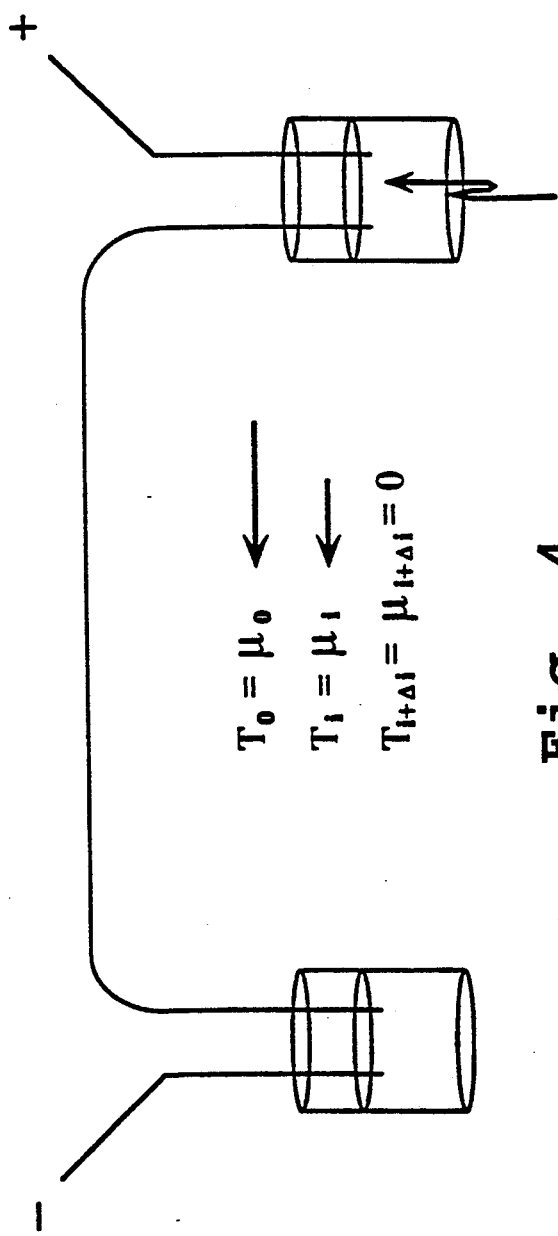
FIG. 4 illustrates the principle of flow-rate controlled surface-charge coating (FCSC) in accordance with the invention.

The principle of the FSCS method is illustrated in FIG. 4. The lines associated with the negative (−) and positive (+) symbols represent the electrodes. The line connecting the two reservoirs represents a capillary tube. T represents the time required to traverse the length of the capillary; $\mu$ represents the electroosmotic flow; and the arrow to the right of $\mu$ represents the vector, indicating the magnitude and direction of electroosmotic flow. At $T_0$, for a given applied voltage, the electroosmotic flow is $\mu_0$. When a positively charged polymer coating agent, for example a quaternary amine containing polymer (see below), is introduced into the anodic reservoir, and a voltage is applied across the tube, the net charge on the tube wall becomes progressively masked by the coating agent, thus reducing the zeta potential and the electroosmotic flow rate through the tube. At some time $T_1$, electroosmotic flow is decreased to $\mu_1$ (denoted as a shorter arrow). Since the electroosmotic flow rate is directly related to the magnitude of the charge on the capillary wall, the slowing in electroosmotic flow with increased run time is the result of the stable coating of the capillary walls by the polymer coating agent, and the resulting net reduction in the charge of the capillary wall. At some point in time, $T_{i+\Delta i}$, the surface charges of the capillary will be neutralized, and the electroosmotic flow, $\mu_{i+\Delta i}$, will be zero.

Figure 5:
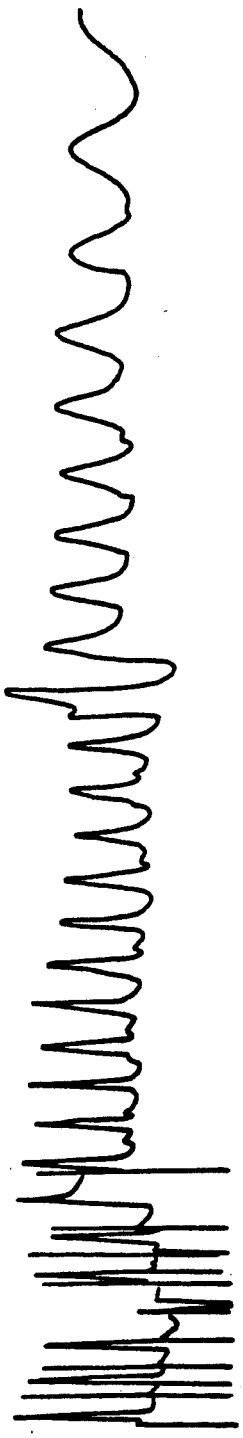
FIG. 5 shows an optical scan of marker pulses introduced at a constant time interval, showing the slowed rate of electroosmotic flow during an FCSC procedure.

FIG. 5 shows an optical scan of marker pulses obtained during a typical FSCS method. Here the polymer coating compound used to stably mask the negative charge of the capillary tube wall was polybrene, a polyquaternary amine having the subunit formula $$[-N^+(R_2)-(CH_2)_6-N^{30}(R_2)-CH_2)_3-]_{2Br}$$

where R is $CH_3$, and the polymer has a molecular weight typically between 5,000–10,000 daltons. Polybrene was included in the anodic electrolyte buffer at a concentration of about 0.0005% (percent by volume).

At periodic, even intervals—in this case, at one-minute intervals—during electroosmotic flow, a marker pulse, typically about 5 nl, is introduced into the anodic end of the tube, and this pulse then travels toward the tube detection zone at a given electroosmotic flow rate. The peaks in FIG. 5 represent the marker pulses observed at the detection zone over a several-minute period. As seen, the distance between marker pulses increases with increasing time (toward the right in the figure), evidencing the decreased electroosmotic flow rate. As noted above, the flow rate at any time period is calculated as the average time of travel of each successive marker pulse.

The average flow rate is monitored in this fashion with continued introduction of the polymer coating agent in the tube, until a desired electroosmotic flow rate is achieved.

Figure 6:
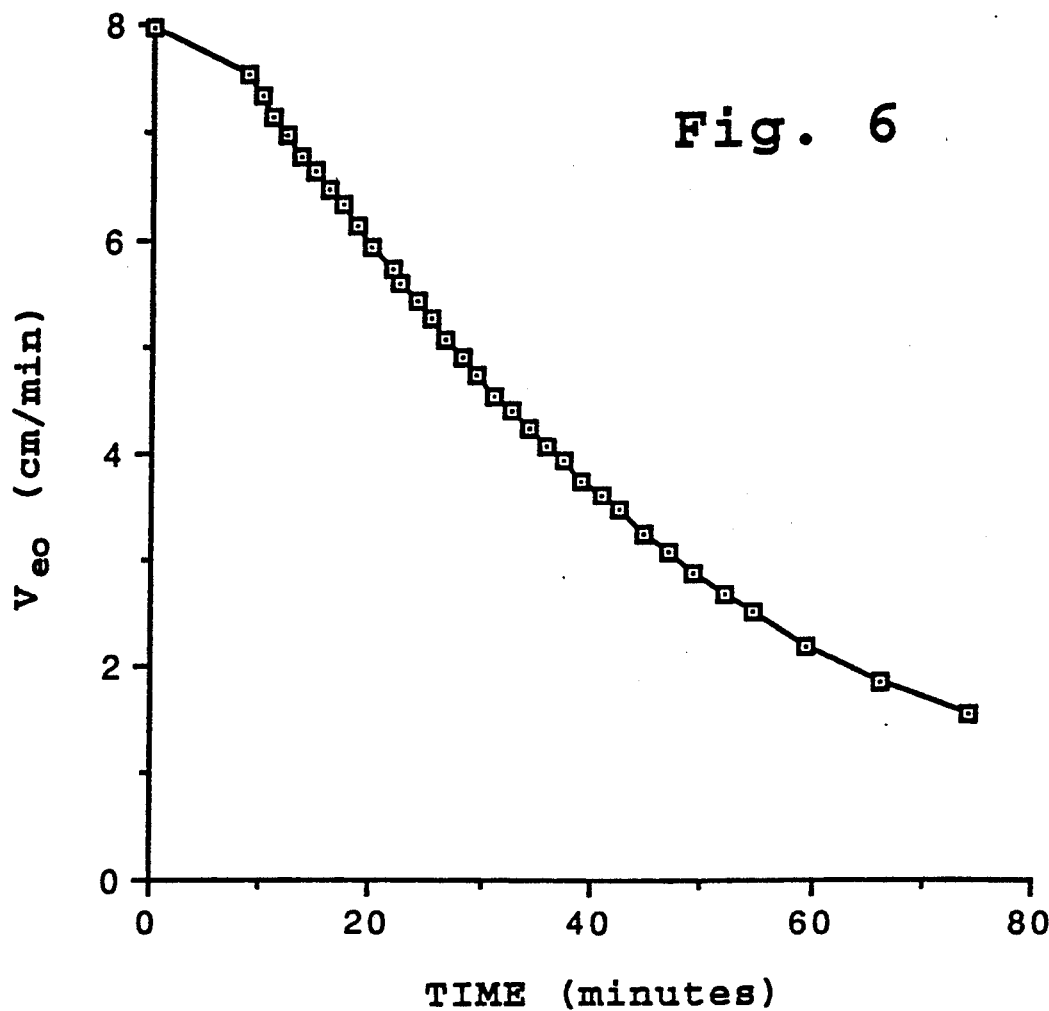
FIG. 6 is a plot of electroosmotic flow rate as a function of coating time with 0.0005% polybrene as coating agent.

FIG. 6 shows a plot of the electroosmotic flow rate $V_{60}$ as a function of coating time, as determined from an optical scan such as that seen in FIG. 5. As seen, $V_{60}$ decreases steadily, over a 60–80 minute period with increased time of exposure of the polymer coating agent to the tube walls, as the agent is drawn into and through the tube by electroosmotic flow. As above, the FIG. 6 curve was obtained using an anodic electrolyte containing 0.0005% polybrene.

Figure 7:
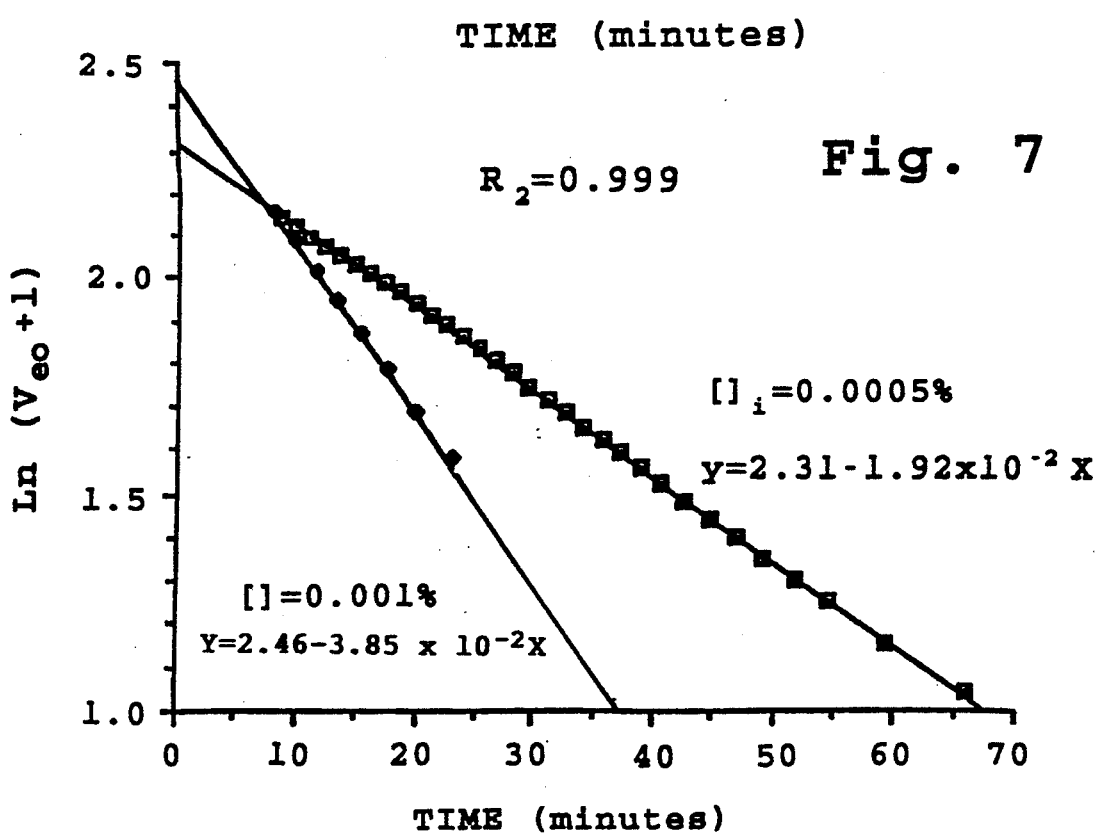
FIG. 7 is a plot of electroosmotic flow rate as a function of coating time using polybrene at two polybrene concentrations as coating agents.

When the natural log of $V_{60}+1$ is plotted against time, a linear curve like those seen in FIG. 7 is obtained. The two curves were obtained at 0.000.5 and 0.001 volume percent polybrene, as indicated. Interestingly, the slope obtained with the 0.001 percent concentration is just twice that obtained at 0.0005 percent, demonstrating a well-defined concentration effect with the polymer agent. Details of the above FCSC method employing polybrene are given in Examples 1 and 2.

At a polybrene concentration of 0.0025 weight percent, a steep plot was obtained, and controlling the electroosmotic flow rate as a function of run time was difficult. It can be appreciated, therefore, that the concentration of polymer coating agent must be such as to alter electroosmotic flow over a relatively extended coating period.

The FCSC method described with respect to FIGS. 5–7 was carried out with polybrene, exemplary of a hydrophobic polyquaternary amine compound. Additional experiments carried out in support of the present invention have shown that polymer coating agents, such as polybrene, are effective to stably alter the charge characteristics of the tube. By this is meant (a) the charge characteristics of the coated tube are stable in the absence of polymer in the electrophoresis medium, and (b) the polymer is removed only by extensive washing and/or treatment with agents, such as surfactants or solvent agents, capable of stripping the polymer coating agent from the wall surface.

Figure 8:
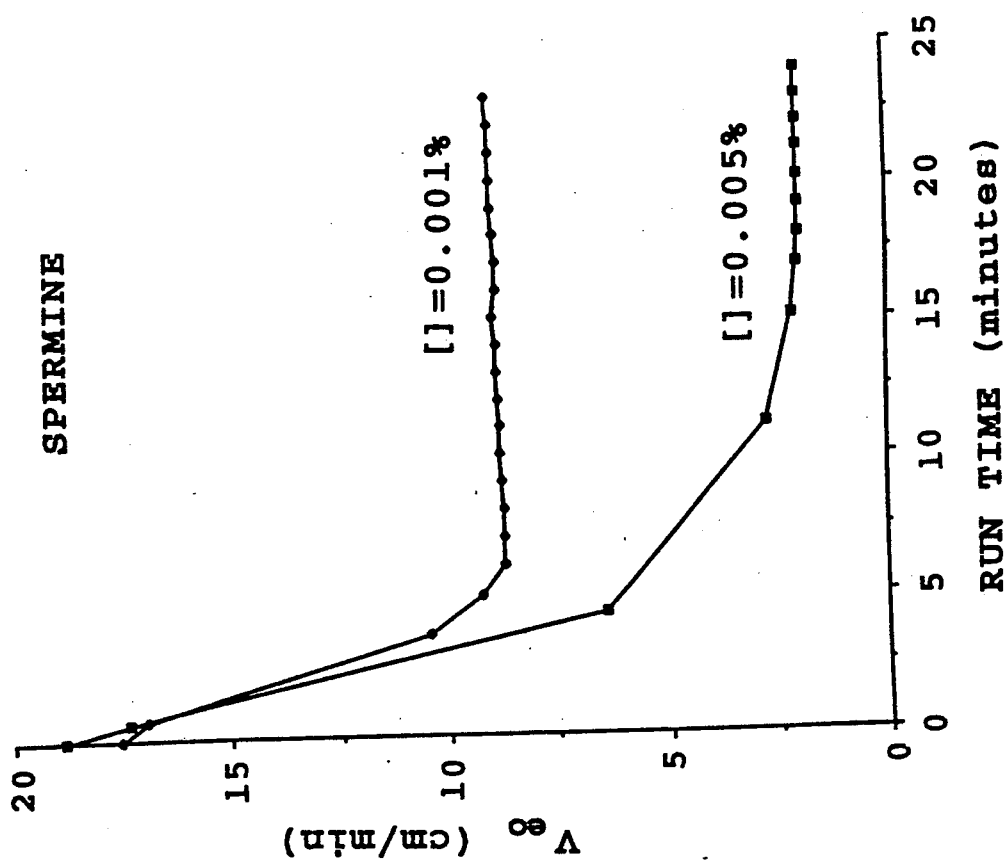
FIG. 8 shows the equilibrium saturation of electroosmotic flow rate as a function of coating time when spermine is used as coating agent.

A number of non-polymer, positively charged compounds have been examined for their ability to produce flow-rate-controlled surface charge coating in a fused silica tube. FIG. 8 shows the effects of FCSC with spermine, a non-polymeric, hydrophilic primary amine, at spermine concentrations of 0.001% and 0.005 volume percent. As seen, the electroosmotic flow ($V_{60}$) as a function of run time plateaus rapidly, indicating that an equilibrium between the capillary-wall-bound spermine and the spermine in the buffer has reached equilibrium. Maintenance of the reduced $V_{60}$ is dependent on the continued presence of spermine in the run buffer and the ionic strength of the buffer. Details of this study are given in Example 3.

Figure 9:
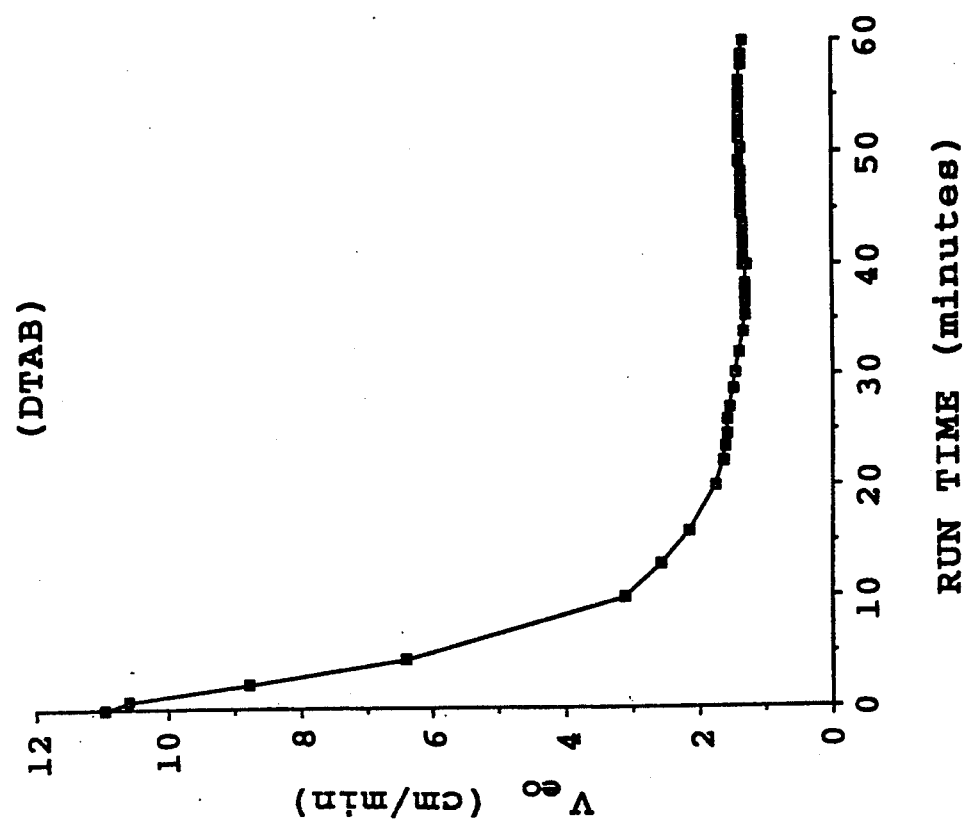
FIG. 9 shows the equilibrium saturation of electroosmotic flow rate as a function of coating time when dodecyl trimethyl ammonium bromide is used as a coating agent.

A second positively charged non-polymeric compound which was examined was dodecyl trimethyl ammonium bromide (DTAB), a non-hydrophobic quaternary amine. The results of time-dependent coating with DTAB, and the accompanying reduction in electroosmotic flow ($V_{60}$) with increasing run time, are shown in FIG. 9. As can be seen from the figure, DTAB, similar to spermine, quickly reaches an equilibrium between the capillary wall bound DTAB and the free DTAB in the buffer. Continued presence of the DTAB was required to maintain the reduced electroosmotic flow rate.

The non-polymer compounds tested above, either hydrophilic or hydrophobic, and either primary or quaternary amines, are thus incapable of stably altering the charge characteristics of the coated tube.

The above results indicate that multiple-site electrostatic, such as occurs with a charged polymer, is necessary for stably masking the surface charge carried on the tube walls.

The charged polymer coating agent used to stably alter surface charge may be either hydrophobic, e.g., polybrene, or relatively hydrophilic. A hydrophobic polymer provides the potential for interacting (binding) between polymer molecules and this binding interaction may be exploited in two ways. First, the capillary tube can be overcoated, for use in producing a net positive charge on the capillary wall, as will be described in Section IV below.

Secondly, the electroosmotic flow of a tube coated (or even overcoated) with a hydrophobic polymer can be controlled by drawing a surfactant or solvent agent, such as ethylene glycol, through the tube by electroosmotic flow, at a surfactant or solvent concentration which causes a gradual removal of hydrophobic polymer from the tube wall, and a concomitant increase in electroosmotic flow. This approach represents a second general embodiment of the invention in which (a) the charge on the capillary tube is due, in part, to a charged polymer coating agent, and (b) the compound used to stably alter the charge on the capillary tube is effective to remove the charged coating at a slow, controlled rate.

In this regard it is noted that when using a hydrophobic polymer coating agent in the FCSC method to partially mask surface charge, it may be necessary to include an agent, such as ethylene glycol, to minimize polymer interaction. For example, in the FCSC procedures described above involving a polybrene coating polymer, the coating solution included 5 volume percent ethylene glycol.

The same considerations discussed above for a capillary tube with negatively charged wall surface groups also apply to a tube with positively charged surface groups, for example, a tube derivatized with amine groups. A stable coating agent suitable for use in reducing surface wall charge is a negatively charged polymer, e.g., a polysulfonic acid, polycarboxylic acid, polyphosphonic acid, or polyphosphoric acid polymer.

Where the negatively charged polymer is hydrophobic, overcoating and selective polymer removal by a surfactant or solvent agent can be incorporated into the method for achieving a desired electroosmotic flow rate, by the FCSC method.

In another general embodiment, the coating agent may be a zwitterionic polymer, i.e., a polymer containing both positive and negative charges Here the relative concentrations of the two charge groups in the coating agent can be adjusted to achieve a desired net charge, and therefore a desired electroosmotic flow rate, at a selected coating level.

The ability to achieve a selected electroosmotic flow rate has important applications to CE separation methods. For example, for any given separation application, appropriate voltage and electroosmotic flow conditions which maximize separation can be determined (see Examples 5-8) and then routinely and reproducibly used to effect CE separation.

Further, for repetitive separation applications, such as in a clinical setting, the capillary tube can be covalently modified to result in a fixed electroosmotic flow. This can be accomplished in one of two ways. First, the capillary tube can be coated with a polymer, such as polybrene, the exposed negatively-charged silane sites can be activated using a bifunctional reagent, then a second coating agent can be applied to the column and covalently attached to the capillary via the bifunctional reagent. Further, the selected flow rate can be established with the polymer, such as polybrene, and then the polymer coating fixed to the capillary tube by dehydration, for example, by baking or chemical dehydration such as by exposure to methanol. Alternatively, the polybrene can be modified to contain a group which can be covalently coupled to the silane group of the capillary wall using a suitable coupling agent.

IV. Applications to Protein Capillary Electrophoresis

A. Overcoating to Block Interactions with the Capillary Wall

A major limitation of the application of capillary electrophoresis to the separation of proteins is that many proteins have a net negative charge, resulting in non-specific protein-binding to the capillary wall. As noted above, reducing pH to protonate the negative groups is impractical, since many proteins are denatured below a pH required for protonation of tube wall charge groups.

Figure 10:
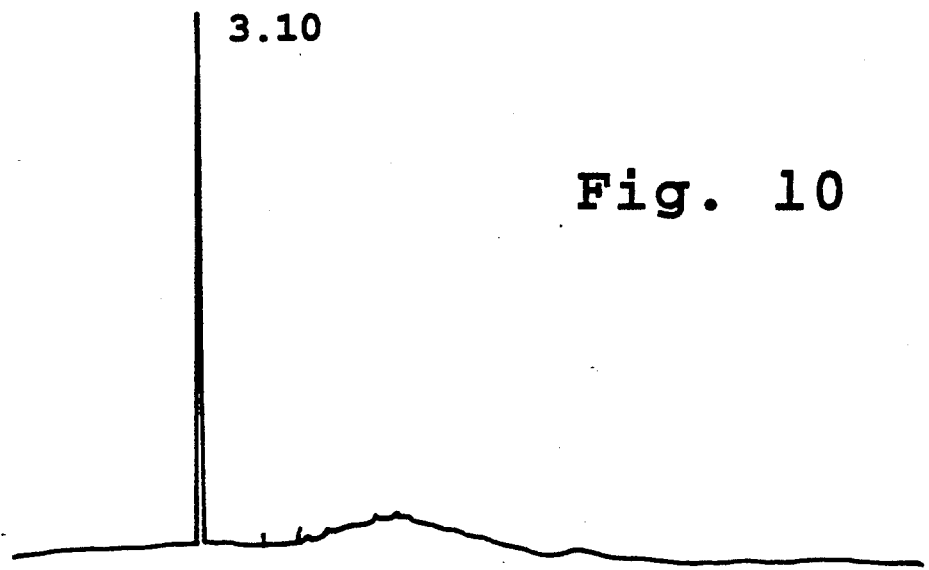
FIG. 10 is an CE electropherogram of lactate dehydrogenase in an uncoated CE tube.

The difficulty of separation of positively charged proteins by CE is demonstrated by the separation procedure described in Example 5 and illustrated in FIG. 10. Three isoforms of lactate dehydrogenase (LDH) derived from rabbit muscle were loaded onto a capillary under the conditions described in Example 5. FIG. 10, which is an electropherogram the CE, shows that there is no recovery of the loaded LDH, indicating that the protein was bound non-specifically to the capillary tube wall.

In order to reverse the charge of the capillary wall, the capillary was over-coated with polybrene. Overcoating with polybrene was accomplished by electrocoating with polybrene at a selected concentration until the electroosmotic flow, $\mu$, decreased to zero. The polymer solution did not contain an agent, such as ethylene glycol, for limiting polymer hydrophobic binding interactions.

At this point, additional polybrene is drawn into the capillary tube by electrophoretic movement only. As additional polybrene is drawn into and through the tube, the tube wall becomes overcoated, due to hydrophobic interactions between the surface-bound polymers, as discussed above. As this occurs, the capillary wall acquires a net positive charge, producing electroosmotic flow in the direction opposite to the flow of polybrene molecules through the tube. The rate of opposite-direction electroosmotic flow (toward the anode) increases as the degree of overcoating increases, and this rate can be monitored, as above, until a desired reverse-direction flow rate is achieved. At some point, the rate of reverse-direction electroosmotic flow will become greater than the rate of electrophoretic movement of the coating agent through the tube, and the electroosmotic flow rate will stabilize.

Electrophoresis of positively charged protein is then carried out by reversing the polarity of the CE system, so that the protein is introduced at the cathodic side of the tube. In this configuration, the direction of electroosmotic flow is in a cathode-to-anode direction, and the electrophoretic migration of positively charged proteins is in the opposite direction. Accordingly, and as described with reference to FIG. 3, the electroosmotic flow rate can be selected, with respect to the opposite-direction electrophoretic migration rate of a selected protein, to optimize separation of that protein from other protein species in the sample.

Figure 11:
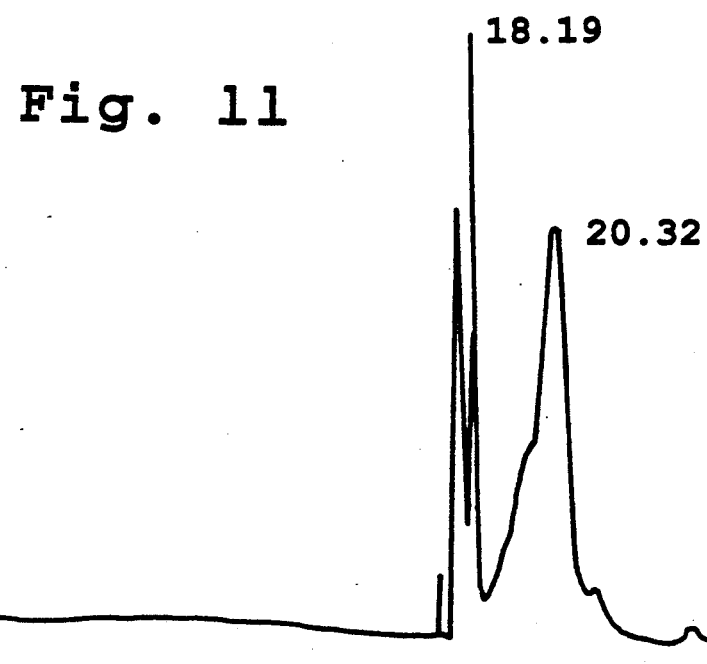
FIG. 11 is a CE electropherogram of lactate dehydrogenase in a CE tube coated with polybrene.

FIG. 11 illustrates the results of a capillary electrophoresis run performed under the same conditions as those used for FIG. 10, but where the capillary was overcoated with polybrene, and the electric field polarity was reversed. As can be seen from FIG. 11, this capillary electrophoresis system, using a capillary tube over-coated with polybrene, provides an extremely efficient separation of the three isoforms of LDH.

Figure 12:
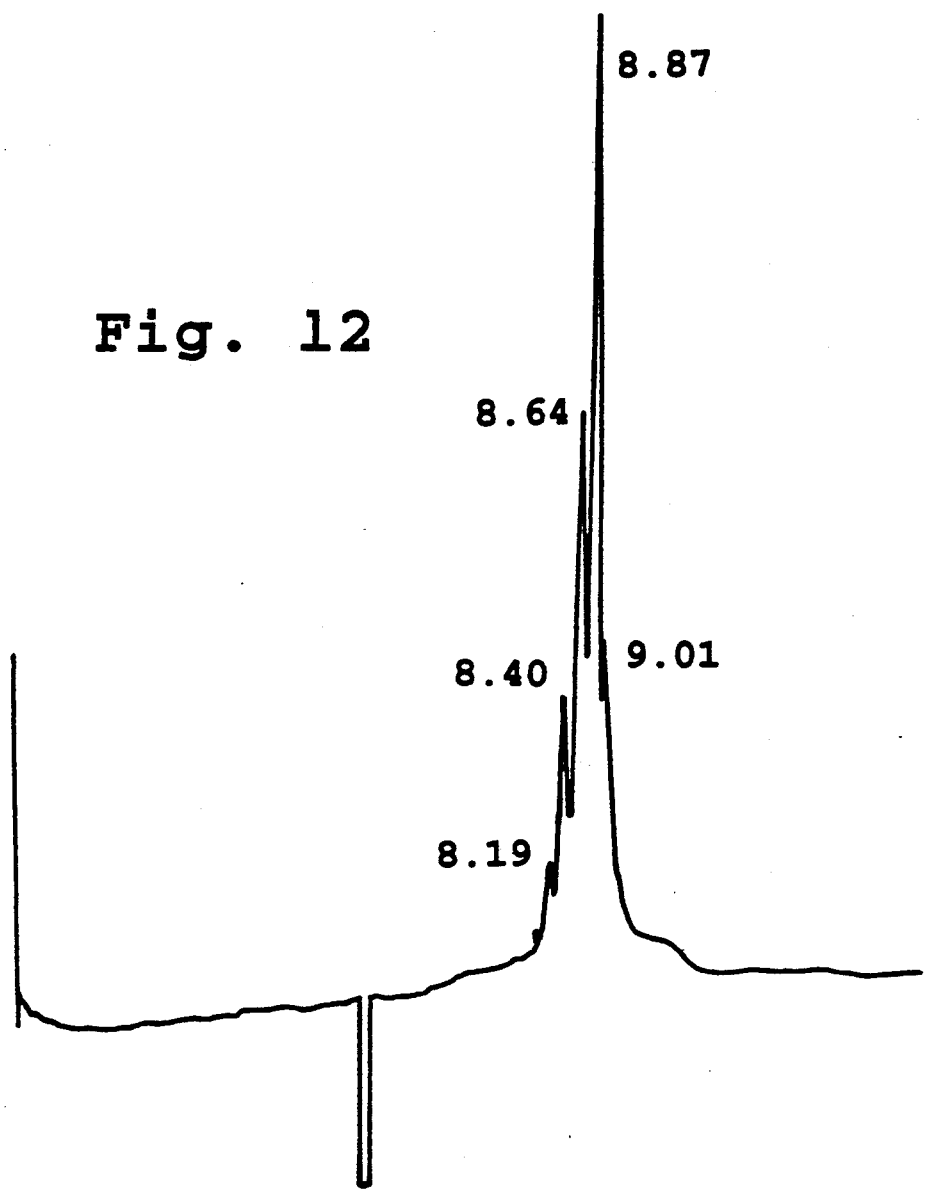
FIG. 12 demonstrates the resolution of five acetylated forms of histone H4 by CE using a polybrene-coated capillary tube.

CE was also performed using, as a sample, the highly basic protein Histone H4 in five acetylated forms. Without overcoating of the capillary with polybrene these proteins do not traverse the capillary. By contrast, when a polybrene over-coated capillary is used for the electrophoresis the system is capable of resolving the five acetylated forms of the protein (Example 5; FIG. 12). Electrophoresis was carried out at pH 6.6.

The ability to separate basic proteins in the capillary electrophoresis system, at pH level of between 4 and 9, provides a valuable technique for the analysis of proteins, particularly when only small quantities of the proteins are available.

B. Capillary electrophoresis of proteins using selected electroosmotic flow rates For negatively charged proteins, no charge-attraction interactions exist between the capillary wall and the protein. The separation of these proteins is thus based on a combination of electroosmotic flow and electrophoretic migration of the proteins in the direction opposing electroosmotic flow. Accordingly, it is useful to be able to adjust electroosmotic flow to optimize protein separation by carrying out the separation at a selected $V_{60}$.

Figure 13:
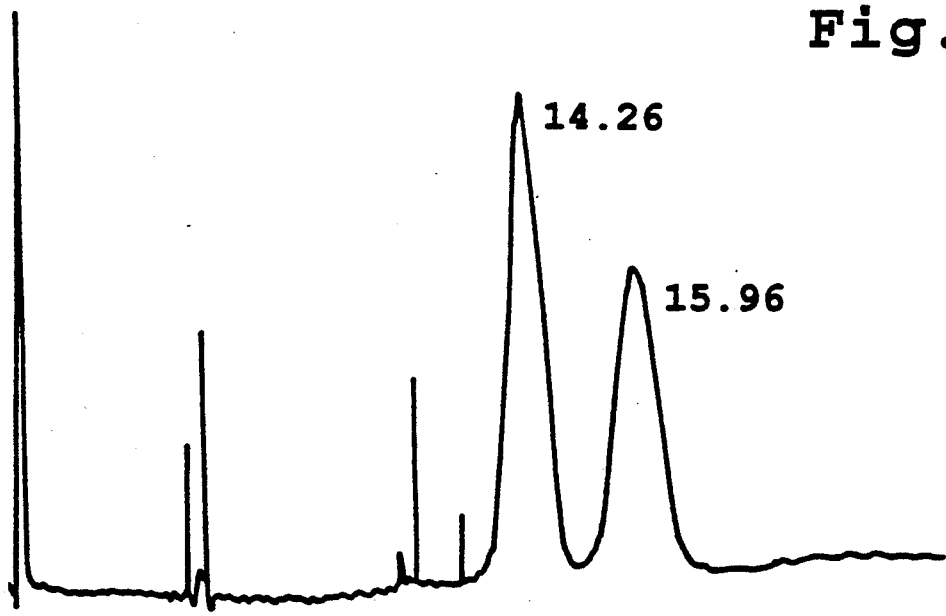
FIG. 13 illustrates the separation of two species of RNase T1.

One example of the use of the FCSC method to achieve separation of a negatively charged protein is shown in FIG. 13 (Example 6). The capillary tube in this example was pre-coated for 5 minutes using 0.001% polybrene and 5% polyethylene glycol minimize hydrophobic interactions which may result in localized unshielded positive charges, followed by loading 2.5 ng of an equal-part mixture of Ribonuclease T1 (RNase T1), which has a net negative charge, and a recombinantly created mutant species having a glutamine to lysine substitution, i.e., one additional positive charge. The electropherogram, shown in FIG. 13, clearly demonstrates the ability of the system to resolve these closely-related proteins. The two species of RNase T1 are the peaks 14.26 and 15.96 in the figure.

C. Ion-exchange Capillary Electrophoresis of Negatively-Charged Proteins

Figure 17:
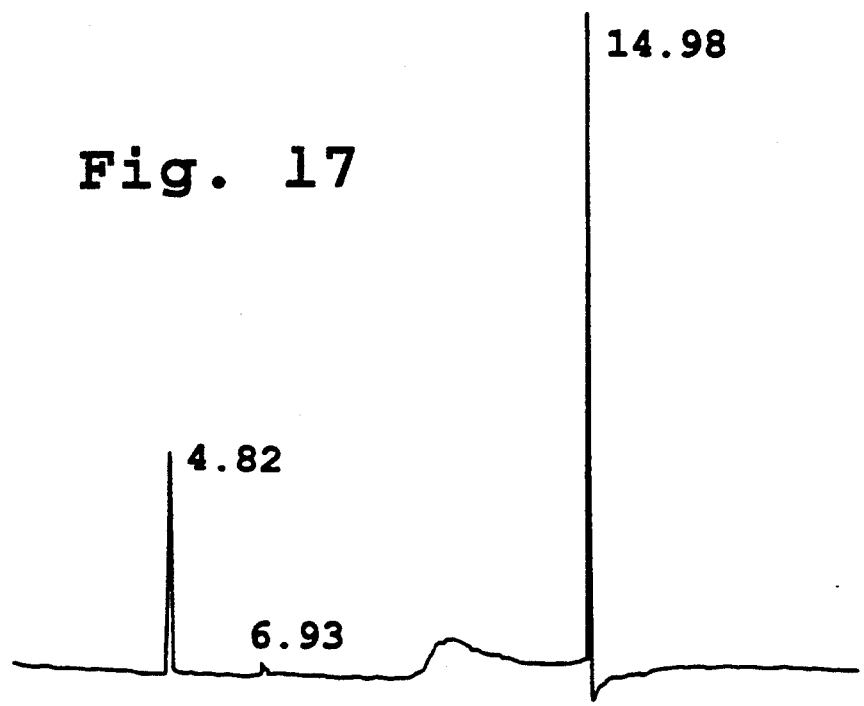
FIG. 17 shows the electropherogram generated from a CE run of two species of RNase T1 in the absence of salt in a capillary tube coated with polybrene.
Figure 18:
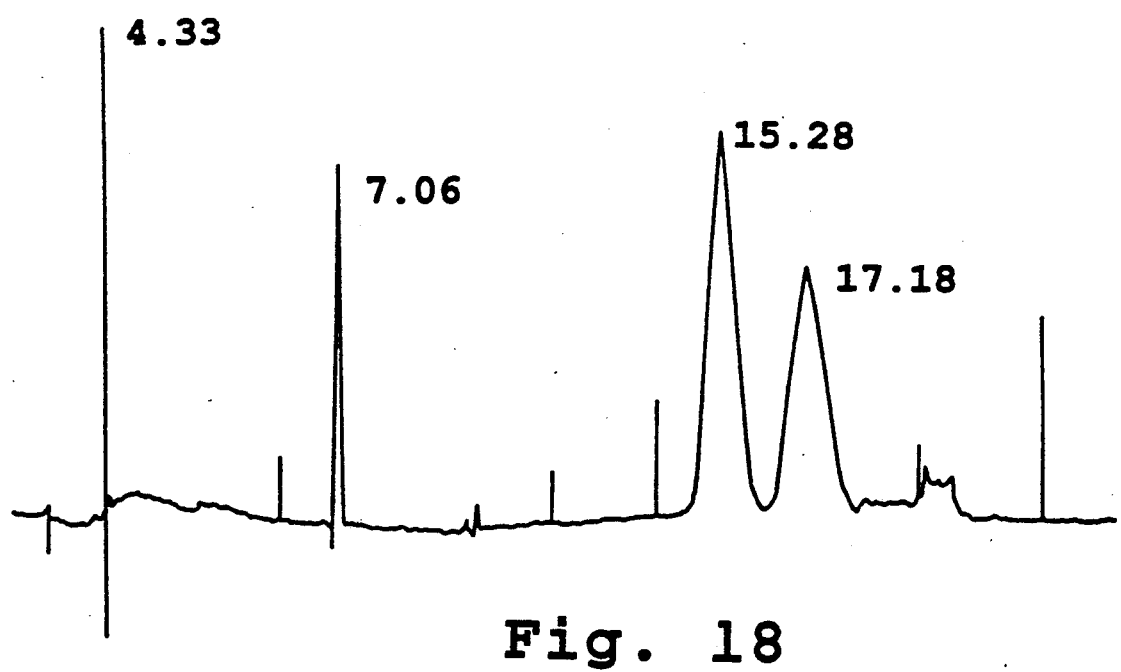
FIG. 18 shows the resolution of the two RNase species in the presence of 30 mM NaCl in a capillary tube coated with polybrene.

Another type of separation which can be achieved using capillary tubes coated in accordance with the present invention involves a competition between salt and the charged protein for charge centers on the capillary wall. This competition is illustrated for RNase T1 and a mutant species (described above) in FIGS. 17 and 18. The capillary tube in this example was partially coated with polybrene, under overcoating conditions (in the absence of ethylene glycol), and the sample mixture of RNase T1 species was loaded on the capillary using 10 mM sodium citrate buffer (pH=6.6) as the electrophoresis buffer (Example 8). The electropherogram resulting from this run is shown in FIG. 17. In this figure, there are no peaks corresponding to either RNase T1 species. The RNase species are, most likely, retained on the column by non-specific charge interactions with the polybrene. When the capillary tube was washed, and the partially coated tube was loaded with the two RNase T1 species in the same buffer plus 10 mM sodium chloride, peaks corresponding to both species were detected. The same method was repeated using increasing concentrations of sodium chloride. The maximum yield of the RNase T1 proteins was obtained with 30 mM NaCl (FIG. 18).

This ability to selectively affect the retention of negatively charged proteins has useful applications to the separation of proteins having differing ionic character. Given a mixture of proteins having differing charge character, coating conditions can be chosen which result in the retention of one or more protein(s) and allow other proteins of the mixture to migrate through the capillary and undergo capillary electrophoretic separation.

A further application of this approach is for concentrating and subsequent separation of negatively-charged proteins; this application of the capillary electrophoresis system is described in Section V for use in concentrating and separating nucleic acid species.

V. Applications to Nucleic Acid Capillary Electrophoresis

The use of CE, in combination with a fluid electrophoresis medium, is disclosed in the above-cited patent application for "Nucleic Acid Fractionation by Counter-Migration Capillary Electrophoresis." Briefly, the method uses a neutral polymer in the electrophoresis buffer to provide a fluid fractionation matrix in the capillary tube. Nucleic acid separation in the method is based on differential migration of the nucleic acid species against the direction of electroosmotic flow, as described above with respect to FIG. 3. Because of molecular interactions of the nucleic acid species with the matrix molecules, the rates of fragment migration toward the anodic reservoir are size-dependent, with smaller fragments migrating faster in the anodic direction (opposite the direction of electroosmotic flow). It can be appreciated that the ability to achieve a selected electroosmotic flow rate, in accordance with the present invention, can be used to optimize separation of the nucleic acid species. The polymer coating compound may be a zwitterion polymer, as described above, for reducing charge interactions with the nucleic acid molecules.

Figure 14:
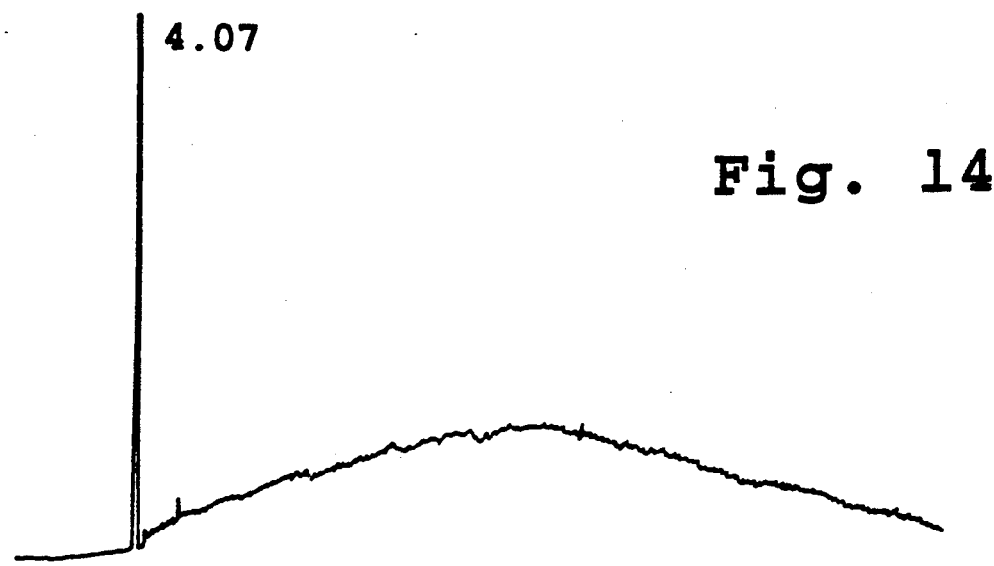
FIG. 14 shows the electropherogram generated from a CE run of DNA in the absence of NaCl in a capillary tube coated with polybrene.
Figure 15:
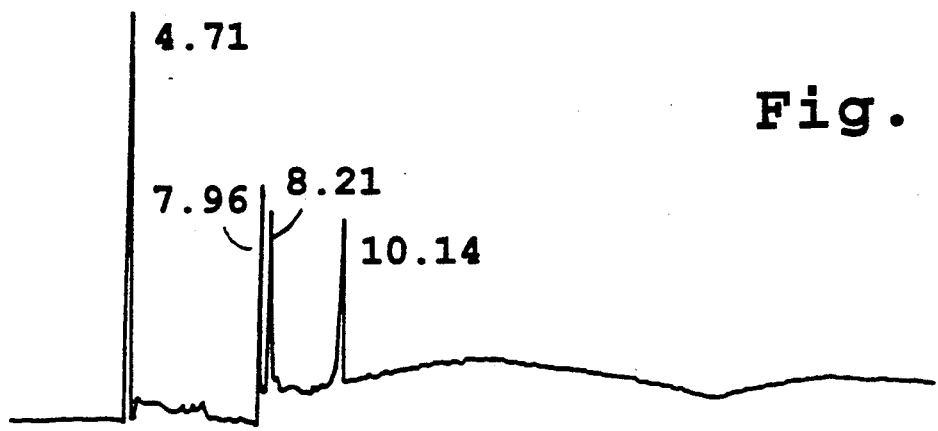
FIG. 15 shows the electropherogram generated from a capillary electrophoresis run of DNA in the presence of 10 mM NaCl in a capillary tube coated with polybrene.
Figure 16:
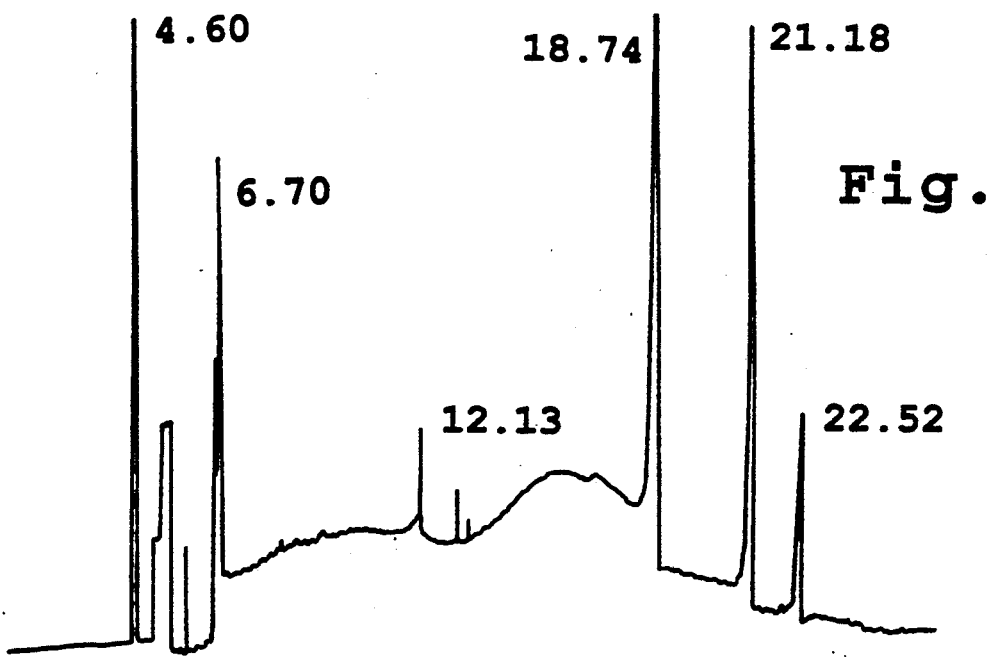
FIG. 16 shows the electropherogram generated from a CE run of DNA in the presence of 20 mM NaCl in a capillary tube coated with polybrene.

Another application of capillary electrophoresis to the separation of nucleic acids is the ion exchange phenomena which was discussed above for negatively charged protein. Example 7 describes the partial coating of a capillary with polybrene and the effects on nucleic acid separation. When a DNA sample was run in SB buffer in the absence of salt no peaks corresponding to the loaded DNA sample were detected (FIG. 14). However, when the same sample was run in the presence of 10 mM NaCl several DNA species were resolved (FIG. 15). Further DNA species were resolved when the salt concentration was increased to 20 mM NaCl (FIG. 16). As for negatively-charged proteins, it appears that the salt is competing for binding to the polybrene resulting in a general ion exchange phenomenon.

The ion exchange phenomenon can be exploited for separation of nucleic acids. Given a mixture of nucleic acid species, conditions can be established such that the larger molecules in the mixture may be bound to the capillary wall allowing more efficient resolution of smaller species in the mixture.

Another application of the ion exchange phenomenon is the ability to concentrate dilute solutions of biologically important macromolecules; this application is important to many clinical and research problems. To concentrate, for example, a dilute sample of nucleic acid, a small portion of the capillary tube is coated with polybrene to result in a net positive charge for the coated region. The dilute sample is then loaded onto the capillary and voltage applied. The nucleic acids bind to and accumulate in the region of polymer coating agent by virtue of ionic interactions. The capillary is then treated with a running buffer of sufficient ionic strength to cause release of the nucleic acid, which occurs in a small zone at the front of the high salt buffer. The released nucleic acids are then resolved by counter-migration capillary electrophoresis, as described above, over the remaining length of the capillary. This method of concentrating macromolecules can be applied to negatively-charged proteins as well.

The following examples illustrate various separation methods and applications in accordance with the invention, but are in no way intended to limit the scope thereof.

EXAMPLE 1

Changes in Electroosmotic Flow as a Function of Polybrene Coating Level

Capillary electrophoresis was carried out using an ABI Model 270 Capillary Electrophoresis System. The system includes a built-in high-voltage DC power supply capable of voltage settings up to 30 KV. The capillary tube used in the system is a fused silica capillary tube 72 cm long with a 50 $\mu$m i.d. and 350 $\mu$m o.d. obtained from Polymicro Technologies (Phoenix, AZ).

The marker used to indicate the rate of electroosmotic flow ($V_{60}$) was the neutral compound, mesityl oxide, which has a strong absorbance at 200 mm. The electrophoretic system was run at a voltage setting of about 25 kV (about 350 V/cm) through the run. UV detection was with a Kratos 783 UV detector designed for capillary tube detection. The detector output signal was integrated and plotted on a Spectrophysics Sp4400 integrator/plotter.

Fresh capillary surface was routinely regenerated by flushing the capillary successively with 5-10 capillary volumes of 1.0 N NaOH, 3-5 volumes $H_2O$, 3-5 volumes 0.1 N HCl, 3-5 volumes $H_2O$, and finally 3-5 volumes of 5 mM Na-$PO_4$ (pH 7.0) buffer. Solutions are drawn through the capillary by virtue of vacuum applied at the cathodic end.

In general, after equilibration with the appropriate buffer, 2-5 nl of neutral marker (mesityl oxide) is injected into the capillary by virtue of vacuum applied at the cathodic end; the marker is used to measure electroosmotic flow. Injection of the marker was followed by injection of 2-5 nl (2-10 ng) of protein sample; either marker or sample may be omitted from the cycle. Appropriate voltage (up to 30 kV) may then be applied across the ends of the capillary and separation monitored via the UV detector. Electrocoating was accomplished by the application of voltage from the anodic reservoir containing buffer plus polybrene (hexadimethrin bromide; available from Applied Biosystems, Foster City, CA) to the cathodic reservoir containing buffer with no polybrene.

Successive injections of marker (2.5 nl) into the capillary followed by one minute pulses of 25 kV result in the migration of the successive marker peaks and anodic buffer with polybrene through the capillary and eventually past the detector. Absorbance at 200 nm was monitored and the average velocity of marker, and therefore the electroosmotic flow, was estimated. There was no detectable absorbance of polybrene under these conditions.

Total run time was about 70 minutes the final approximately 50 minutes are shown in FIG. 5. The concentration of polybrene in the anodic reservoir was 0.0005% volume percent. At approximately 24 minutes the polybrene had migrated the entire length of the capillary tube. The slowing of the electroosmotic flow rate is apparent from the increasing distance between the neutral marker peaks which occurs as the run progresses and the capillary becomes progressively more coated with the polybrene.

EXAMPLE 2

Calibrating Electroosmotic Flow Rates

The same capillary electrophoretic conditions used in Example 1 were employed. The rate of electroosmotic flow ($V_{60}$ represented in cm/min) was calculated based on the distance traversed and the time elapsed from injection of the neutral marker until the pulse passed the UV detector. The calculated $V_{60}$ was plotted against the total elapsed run time; the results are represented in FIG. 6. Polybrene at a concentration of 0.0005% was present in the anionic reservoir at time 0.

Electrocoating using polybrene at a concentration of 0.001% was also performed. The Ln of ($V_{60}+1$) was plotted against the total elapsed run time for the polybrene concentrations of 0.0005% and 0.001% (FIG. 7). As can be seen from FIG. 7 at these polybrene concentrations a reliable relationship is established between coating time, the concentration of the polymer and the electroosmotic flow rate. For example, the same $V_{60}$ can be established by coating with 0.001% polybrene for approximately 25 minutes versus coating with 0.0005% polybrene for approximately 42 minutes.

EXAMPLE 3

Calibrating Electroosmotic Flow Rate Using a Non-Polymeric Primary Amine

The same capillary electrophoretic conditions used in Example 1 were employed and $V_{60}$ was calculated as above. spermine, a non-polymeric primary amine, was used as the coating agent at concentrations of 0.001% and 0.005% and its affects on $V_{60}$ with increasing run time are shown in FIG. 8. As can be seen from FIG. 8 the $V_{60}$ plateaus rapidly with spermine relative to polybrene (FIG. 6); this results in less sensitivity for calibration of $V_{60}$ with spermine. A further limitation of spermine is that it can be removed by ions in the electrophoresis buffer.

EXAMPLE 4

Calibrating Electroosmotic Flow Rate Using a Non-Polymeric Quaternary Amine

The same capillary electrophoretic conditions used in Example 1 were employed and $V_{60}$ was calculated as above. Dodecyl trimethyl ammonium bromide (DTAB), a non-polymeric quaternary amine, was used as the coating agent at a concentration of 0.15% and the effects on $V_{60}$ are represented in FIG. 9. DTAB has one of the same limitations as spermine, in that, relative to polybrene DTAB plateaus rapidly, thus calibration of $V_{60}$ using DTAB is not as sensitive as polybrene.

EXAMPLE 5

CE Electrophoresis of Proteins

A. Lactate Dehydrogenase

Capillary electrophoresis was performed as described in Example 1. Approximately 2.5 ng of lactate dehydrogenase (LDH) from rabbit muscle containing three isoforms (pI=8.3, 8.4, 8.55) was loaded in 5 mM $NaPO_4$ buffer (pH=7.0) with the addition of 2.5 nl of the neutral marker. In the absence of polybrene coating only the neutral marker was seen to flow through the column. FIG. 10 shows the results of the run in the absence of polybrene coating of the capillary; the single peak at 3.10 mins. is the neutral marker.

FIG. 11 shows the results of a similar run where the capillary tube has been pre-coated using 0.01% polybrene for 10 minutes; this degree of pre-coating results in over-coating of the capillary tube, reversal of the negative charge on the capillary surface, and the concomitant reversal of direction of electroosmotic flow. The polarity of the electrodes was reversed before loading of the protein sample. No polybrene was present in the electrophoresis buffer and 2.5 ng of LDH isoforms were loaded. The results of the LDH run in the presence of polybrene overcoating is shown in FIG. 11. The peaks at 17.82 (immediately preceding the 18.19 peak), 18.19, and 20.32 correspond to the 8.3, 8.4 and 8.55 isoforms, respectively. The shoulder at 19.68 represents a contaminant of the preparation, possibly formed as the result of storage of the LDH. As can be seen from comparison of FIGS. 10 and 11 effective separation can only be achieved with LDH when the capillary has been coated with polybrene.

B. Acetylated Histone H4

Capillary electrophoresis was performed as described in Example 1. The capillary was over-coated with polybrene as above to establish an electroosmotic flow rate of 5.51 cm/min. The polarity of the electrodes was reversed before loading the proteins. The electrophoresis buffer was 10 mM Na-citrate, pH=6.6; the running buffer did not contain additional polybrene. Approximately 3.0 ng of multiply acetylated histone H4's, containing 0–4 acetyl groups, was loaded for the run. FIG. 12 shows the ability of the system to resolve the five acetylated forms of H4. The proteins corresponding to the peaks shown in the electropherogram are as follows (peak/number of acetyl groups): 9.01/0; 8.87/1; 8.64/2; 8.4/3; and, 8.19/4. Without coating these highly basic proteins do not traverse the capillary but remain attracted to the capillary surface (data not shown).

EXAMPLE 6

Protein Separation by CE as a Function of Electroosmotic Flow Rate

A. Capillary tube preparation for selected electroosmotic flow rates

The capillary tubes were prepared by pre-coating the capillary for 5 min using 0.001% polybrene in 5 mM $Na-PO_4$ (pH 7.0) buffer containing 5% ethylene glycol.

B. Separation of two species of Ribonuclease T1

Capillary electrophoresis was performed as described in Example 1. The pre-coated capillary described in section A was used. The running buffer was 5 mM $Na-PO_4$ (pH=7) with the addition of 20 mM NaCl; no additional polybrene was added to the running buffer. An equal part mixture was prepared of wild-type *Aspergillus oryza* Ribonuclease T1 (RNase T1) and a recombinant mutant species having a glutamine to lysine substitution; this substitution results in the mutant having one more positive charge than wild-type. Approximately 2.5 ng of the protein mixture was loaded and separation carried out for 16 minutes at 25 kV. The neutral marker is represented by the peak at 6.67. No loss in coating is observed under these conditions.

The exquisite sensitivity of this separation system can be seen in the two well defined peaks (14.26 and 15.96; FIG. 13) corresponding to the two species of RNase T1. The very sharp spikes are correspond to precipitates formed in the running buffer; this precipitate can be eliminated by pre-filtration, but its presence does not affect separation.

EXAMPLE 7

Ion-Exchange Electrophoresis of Nucleic Acid

Capillary electrophoresis was performed as in Example 1 except the capillary was electrocoated with polybrene before loading of the DNA sample and the buffer was SB (5 mM Na-borate (pH=9) containing 0.15% hydroxyethyl cellulose).

The extent of electrocoating was monitored as described in Example 1. Electrocoating was allowed to proceed for five minutes in SB, with polybrene at a concentration of 0.001%, which under these conditions resulted in a decrease in endoosmotic velocity of 29% (from 17.0 cm/min to 13.1 cm/min). DNA peaks were monitored at 260 nm.

Three nanograms of DNA (1kb ladder obtained from Bethesda Research Lab.) was loaded onto the column and in the course of a 30 minute run no DNA peaks were detected (FIG. 14).

The capillary was then washed with the SB buffer plus 10 mM NaCl. DNA was loaded and run as above, using SB +10 mM NaCl as running buffer. As can be seen from FIG. 15, several DNA peaks were then detected during the 30-min run. The capillary was washed with the SB buffer plus 20 mM NaCl. DNA was loaded and run as above, using SB +20 mM NaCl as running buffer; more DNA species were detected (FIG. 16). It is apparent from comparing these two figures that specific DNA species can be released in an ion exchange fashion using, in this case, a step gradient. FIGS. 15 and 16 show that peaks are sharp and the DNA fragments are well resolved.

EXAMPLE 8

Ion-Exchange Capillary Electrophoresis (ICE) of Anionic Proteins

Partial coating of the capillary was achieved with 10 mM Na-Citrate buffer (pH 6.6) essentially as described in Example 7, but minus ethylene glycol. Ribonuclease T1 (pI=2.9) and a mutant species of RNase T1, differing by one positive charge (see Example 6), were loaded onto a capillary, under vacuum. The capillary electrophoretic conditions were as described in Example 1. FIG. 17 shows the results of the run; the peak at 4.82 is the neutral marker and the spike at 14.98 indicates the end of the run. There is an absence of a definable peak at 200 nm which would correlate to RNase T1.

At pH=6.6 RNase T1 and the mutant T1 are negatively charged. When the capillary was washed with the 10 mM Nacitrate buffer +10 mM NaCl and more protein was applied two peaks appeared. Recovery increased as the same amount of protein was loaded with increasing salt concentration until a maximum yield of protein was obtained at 30 mM NaCl (FIG. 18).

While the invention has been described with respect to specific embodiments, methods, and applications, it will be recognized by those skilled in the art that modifications of the methods and application of the methods to other uses involving the separation of macromolecules may be made without departing from the invention.

IT IS CLAIMED:

1. A method of achieving selected electroosmotic flow characteristics in a capillary tube having charged surface groups, comprising
   placing opposite ends of the tube in anodic and cathodic electrolyte reservoirs,
   applying an electric field across the two reservoirs to produce electroosmotic flow from one tube end toward the other tube end,
   drawing into and through the tube, a compound capable of stably altering the surface charge of the tube, as the compound is drawn through the tube,
   monitoring the electroosmotic flow rate within the tube as the compound is drawn into and through the tube, and
   continuing to draw said compound into and through the tube until a desired electroosmotic flow rate in the tube, as determined from said monitoring, is achieved.

2. The method of claim 1, wherein said monitoring includes introducing into said tube, at spaced time intervals, a plurality of pulses of a flow marker solution whose travel through the tube can be used to monitor the electroosmotic flow rate of a band of fluid in the tube containing the marker solution.

3. The method of claim 1, wherein said tube is a quartz glass tube having negatively charged surface silane groups, and said compound is a polymer containing regularly spaced, charged amine groups.

4. The method of claim 2, wherein the polymer is a quaternary amine, hydrophobic polymer.

5. The method of claim 4, wherein the polymer is polybrene.

6. The method of claim 1, wherein the tube is a quartz glass tube having positively charged amine groups, and said compound is a negatively charged polymer selected from the group consisting of a polysulfonic acid, polycarboxylic acid, polyphosphonic acid, and polyphosphoric acid polymer.

7. The method of claim 1, wherein the charged surface groups are due in part to molecules of a charged coating agent which is bound to the surface walls electrostatically, and said compound is effective to promote removal of the coating agent molecules from the surface walls, as the compound is drawn through the tube.

8. The method of claim 1, wherein the compound is a charged polymer compound which is effective to bind to the surface walls of the tube electrostatically and to itself hydrophobically, as the compound is drawn into and through the tube, said drawing includes drawing the compound into the tube in the initial direction of electroosmotic flow, until the charge on the surface walls is neutralized and electroosmotic flow in said initial direction ceases, and further drawing the charged polymer compound through the tube in the same direction until electroosmotic flow within the tube, in the opposite direction, reaches a selected rate.

9. The method of claim 8, wherein said capillary tube walls have negative charges, and the charged polymer compound is a hydrophobic quaternary amine polymer.

10. The method of claim 1, for use in preparing a capillary electrophoresis tube for use in separating at least two macromolecular species having different size properties or charge properties or both in a selected electrophoresis medium, wherein the electroosmotic flow characteristics are selected to enhance the degree of separation between the macromolecules which can be achieved by capillary electrophoresis in the selected medium.

11. The method of claim 10, for use in separating positively charged proteins, wherein said surface walls have negatively charged groups, and said compound is a hydrophobic polyamine polymer which is effective to bind to the surface walls of the tube electrostatically and to itself hydrophobically, as the compound is drawn into and through the tube, said drawing includes drawing the compound into the tube in the initial direction of electroosmotic flow, until the negative charge on the capillary surface walls is at least substantially neutralized.

12. The method of claim 11, wherein said drawing is continued until electroosmotic flow in the initial direction ceases, and further includes drawing the compound through the tube in said initial direction until electroosmotic flow within the tube, in the opposite direction, reaches a selected rate.

13. The method of claim 10, for use in separating nucleic acid species, wherein said capillary surface walls have negatively charged groups, and said compound is a hydrophobic polyamine polymer, which further includes electrophoretically separating the nucleic acid species in an electrophoretic medium whose ionic strength at which at least one of the species to be separated does not bind to the polymer compound on the capillary surface walls.

14. The method of claim 13, wherein the ionic strength of the electrophoretic medium is such as to cause preferential binding of the different nucleic species to the polymer bound to the capillary surface walls.

15. The method of claim 1, which further includes attaching the compound to the capillary surface walls, by dehydrating, by baking or by a chemical means.

16. The method of claim 1, for use in producing a capillary tube having a selected density of covalently attached charged groups on the surface of the capillary wall, wherein said compound contains chemical groups which can be covalently linked to surface wall groups, which further includes coupling the compound covalently to the surface walls.

* * * * *